(12) United States Patent
Tsuge (10) Patent No.: US 12,238,627 B2
(45) Date of Patent: Feb. 25, 2025

(54) VEHICLE WITH EMERGENCY REPORTING FUNCTION, AND VEHICLE EMERGENCY REPORTING SYSTEM

(71) Applicant: SUBARU CORPORATION, Tokyo (JP)

(72) Inventor: Masatoshi Tsuge, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 351 days.

(21) Appl. No.: 17/854,888

(22) Filed: Jun. 30, 2022

(65) Prior Publication Data

US 2023/0021809 A1 Jan. 26, 2023

(30) Foreign Application Priority Data

Jul. 21, 2021 (JP) .................................. 2021-120768

(51) Int. Cl.
| | |
|---|---|
| *G01M 17/00* | (2006.01) |
| *B60R 21/013* | (2006.01) |
| *G06F 21/62* | (2013.01) |
| *G08B 25/10* | (2006.01) |
| *G16H 10/60* | (2018.01) |
| *H04W 4/90* | (2018.01) |

(52) U.S. Cl.
CPC ............. *H04W 4/90* (2018.02); *B60R 21/013* (2013.01); *G06F 21/6218* (2013.01); *G08B 25/10* (2013.01); *G16H 10/60* (2018.01)

(58) Field of Classification Search
CPC .......... H04W 4/90; G16H 10/60; G16H 40/63; G16H 15/00; G16H 30/40; B60R 21/013; G06F 21/6218; G08B 25/10; G06Q 50/40; G06Q 50/22; G06Q 10/08
See application file for complete search history.

(56) References Cited

U.S. PATENT DOCUMENTS

| | | | |
|---|---|---|---|
| 10,165,429 B1 * | 12/2018 | Young .................... | H04W 4/90 |
| 2018/0029553 A1 | 2/2018 | Hamakami | |
| 2021/0099849 A1 * | 4/2021 | Zoidl ................ | B60W 60/0016 |

FOREIGN PATENT DOCUMENTS

| | | |
|---|---|---|
| JP | 11-219488 A | 8/1999 |
| WO | 2016/170610 A1 | 10/2016 |

* cited by examiner

*Primary Examiner* — Adam M Alharbi
(74) *Attorney, Agent, or Firm* — Rimon P.C.

(57) ABSTRACT

A vehicle with an emergency reporting function transmits an emergency report in a case where the vehicle is involved in an emergency. The vehicle includes a vehicle communicator and a vehicle memory. The vehicle communicator transmits the emergency report to an operator terminal. The operator terminal acquires emergency-related information by accessing a memory holding the emergency-related information. The emergency-related information includes limited-access information about the vehicle, an occupant of the vehicle, or both. The vehicle memory holds authentication information to be used to access the limited-access information held in the memory. The vehicle communicator transmits the authentication information to the operator terminal, and causes the operator terminal to acquire the limited-access information from the memory, as a part of the emergency-related information, by using the authentication information received from the vehicle.

18 Claims, 6 Drawing Sheets

| VEHICLE IDENTIFICATION INFORMATION | BASIC INFORMATION | LINK INFORMATION |
|---|---|---|
| BRZ-001 | OWNER NAME, CONTACT INFORMATION, ADDRESS | Owner1 |
| XV-001 | OWNER NAME, CONTACT INFORMATION, ADDRESS | Owner2, Group1 |
| ⋮ | ⋮ | ⋮ |

| VEHICLE IDENTIFICATION INFORMATION | AUTHENTICATION INFORMATION OF FILE | |
|---|---|---|
| | ID (FILE NAME) | PASSWORD |
| BRZ-001 | Owner1 | Pass001 |

VEHICLE WITH EMERGENCY REPORTING FUNCTION, AND VEHICLE EMERGENCY REPORTING SYSTEM

CROSS-REFERENCE TO RELATED APPLICATIONS

The present application claims priority from Japanese Patent Application No. 2021-120768 filed on Jul. 21, 2021, the entire contents of which are hereby incorporated by reference.

BACKGROUND

The technology relates to a vehicle with an emergency reporting function, and to a vehicle emergency reporting system.

A vehicle, such as an automobile, can come into collision with another automobile while traveling, or an occupant of the automobile can feel sick. In this case, the automobile makes an emergency report to an operator of an emergency support center. For example, reference is made to Japanese Unexamined Patent Application Publication No. H11-219488 and International Publication No. WO 2016/170610.

In response to an emergency report, the operator of the emergency support center makes a dispatch request of a dispatch team. The dispatch team rushes to a site where the automobile that has made the emergency report is present by an emergency vehicle, for example, to execute an emergency response.

This enables the automobile and the occupant involved in an emergency to receive the emergency response.

SUMMARY

An aspect of the technology provides a vehicle with an emergency reporting function. The vehicle is configured to transmit an emergency report in a case where the vehicle is involved in an emergency. The vehicle includes a vehicle communicator and a vehicle memory. The vehicle communicator is configured to transmit the emergency report to an operator terminal. The operator terminal is configured to acquire emergency-related information by accessing a memory holding the emergency-related information. The emergency-related information includes limited-access information about the vehicle, an occupant of the vehicle, or both. The vehicle memory is configured to hold authentication information to be used to access the limited-access information held in the memory. The vehicle communicator is configured to transmit the authentication information to the operator terminal, and cause the operator terminal to acquire the limited-access information from the memory, as a part of the emergency-related information, by using the authentication information received from the vehicle.

An aspect of the technology provides a vehicle emergency reporting system to be applied to a vehicle. The vehicle emergency reporting system is to be used in a case where the vehicle is involved in an emergency. The vehicle emergency reporting system includes a server, an operator terminal, and the vehicle. The server includes a server memory configured to hold emergency-related information including limited-access information about the vehicle, an occupant of the vehicle, or both. The operator terminal is configured to acquire the emergency-related information held in the server memory by accessing the server. The vehicle includes a vehicle communicator configured to transmit an emergency report to the operator terminal. The vehicle includes a vehicle memory configured to hold authentication information to be used to access the limited-access information held in the server memory. The vehicle is configured to transmit the authentication information from the vehicle communicator to the operator terminal. The operator terminal is configured to, in a case where the operator terminal receives the emergency report from the vehicle, acquire the limited-access information from the server memory of the server, as a part of the emergency-related information, by using the authentication information received from the vehicle.

BRIEF DESCRIPTION OF THE DRAWINGS

The accompanying drawings are included to provide a further understanding of the disclosure and are incorporated in and constitute a part of this specification. The drawings illustrate example embodiments and, together with the specification, serve to explain the principles of the technology.

DETAILED DESCRIPTION

In an emergency response, it is desired to take an action or a measure corresponding to details of an emergency. In a case where emergency response personnel finds a shortage of equipment, for example, after arriving at a site, it is difficult for the emergency response personnel who has rushed to the site to immediately start the emergency response.

For a more appropriate emergency response, it is thus desired that, before making a dispatch request of a dispatch team, an operator of an emergency support center inquire, by phone, about details and a degree of an emergency of an occupant of an automobile from which an emergency report has been received.

However, even if it is possible to inquire about details of an emergency by such inquiry by phone, it is impractical to inquire about further details under a situation demanding an emergency response. For example, it is impractical to inquire about a medical history, for example, of the occupant of the automobile involved in the emergency in an emergency phone call. In addition, in a case where the occupant is unconscious, it is difficult to inquire of the occupant by phone.

It is desirable to provide a vehicle with an emergency reporting function and a vehicle emergency reporting system that allow for a more appropriate emergency response.

Some example embodiments of the technology will now be described in detail with reference to the accompanying drawings. Note that the following description is directed to illustrative examples of the technology and not to be construed as limiting to the technology. Factors including, without limitation, numerical values, shapes, materials, components, positions of the components, and how the components are coupled to each other are illustrative only and not to be construed as limiting to the technology. Further, elements in the following example embodiments that are not recited in a most-generic independent claim of the technology are optional and may be provided on an as-needed basis. The drawings are schematic and are not intended to be drawn to scale. Throughout the present specification and the drawings, elements having substantially the same function and configuration are denoted with the same numerals to avoid any redundant description.

First Example Embodiment

Figure 1:
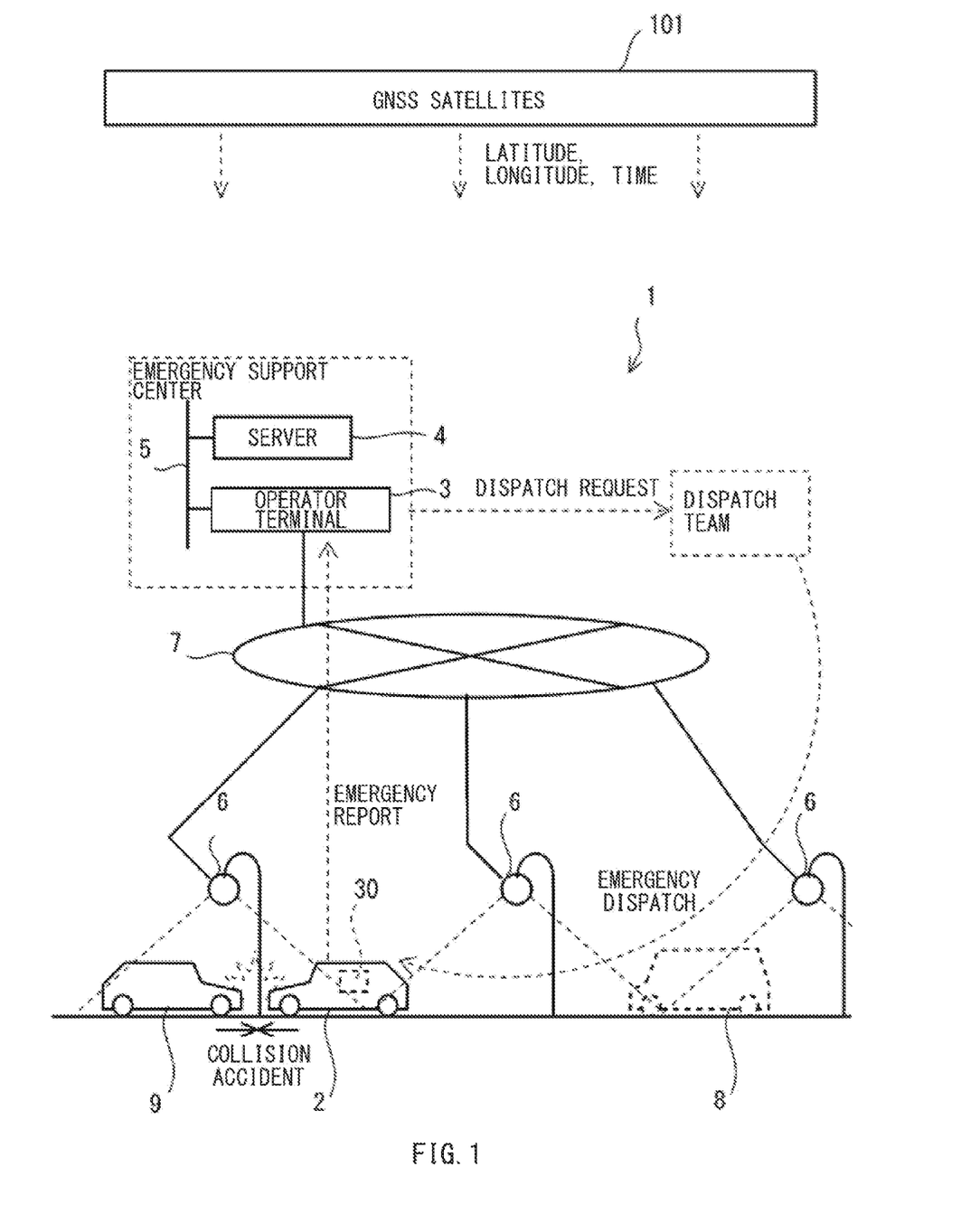
FIG. 1 is an explanatory diagram illustrating an automatic emergency reporting system for an automobile, according to one example embodiment of the technology.

FIG. 1 is an explanatory diagram illustrating an automatic emergency reporting system 1 for an automobile, according to a first example embodiment of the technology.

The automatic emergency reporting system 1 illustrated in FIG. 1 may include an automobile 2 supporting the system, and an operator terminal 3 and a server 4 of an emergency support center.

The automobile 2 (hereinafter also referred to as an own vehicle) is an example of a vehicle that is able to travel while carrying an occupant. A control system 30 of the automobile 2 may establish, via a mobile communicator 33 to be described later, a communication path with a base station 6 among a plurality of base stations 6. The base station 6 may include, in its zone, a road on which the automobile 2 travels. The plurality of base stations 6 may be coupled to a communication network 7. The base station 6 and the communication network 7 may be a 5G base station and a 5G communication network provided by a carrier. In another example, the base station 6 and the communication network 7 may be an advanced driver assistance system (ADAS)-dedicated base station and an ADAS-dedicated communication network provided by, for example, a public institution.

The operator terminal 3 may be coupled to the communication network 7 and to a local area network 5 of the emergency support center, via a communication device 17 to be described later. The server 4 may be coupled to the local area network 5.

The automobile 2 can come into collision with another automobile 9 while traveling, or an occupant, such as an owner who drives the automobile 2, can feel sick. In a case where the automobile 2 is thus involved in an emergency, the control system 30 of the automobile 2 may make an emergency report to the operator terminal 3 of the emergency support center from the mobile communicator 33 to be described later, through the base station 6 and the communication network 7. In one embodiment, the owner may serve as a "driver".

An operator of the emergency support center may check the emergency report received by the operator terminal 3, and make a dispatch request of a dispatch team. The dispatch team may rush to a site where the automobile 2 that has made the emergency report is present, by an emergency vehicle 8, to execute an emergency response.

This enables the automobile 2 and the occupant involved in the emergency to receive the emergency response executed by the dispatch team.

In an emergency response, it is desired to take an action or a measure corresponding to details of an emergency. For example, if a shortage of equipment occurs after arriving at a site, emergency response personnel has to wait for preparation of the equipment. This makes it difficult for the emergency response personnel that has rushed to the site to start the emergency response immediately after arriving at the site.

For a more appropriate emergency response, it may thus be desired that, before making a dispatch request of a dispatch team, the operator of the emergency support center talk by phone with the occupant of the automobile 2 from which an emergency report has been received, to grasp details and a degree of an emergency in advance.

However, even if the operator is able to inquire about details of an emergency by phone, it is impractical to inquire about further details under a situation demanding an emergency response. For example, the operator is not always able to inquire about a medical history of the occupant of the automobile 2 involved in an emergency in each emergency phone call. In addition, even if the operator places a phone call, an occupant who has lost consciousness due to an accident, for example, is unable to respond to the phone call.

As described above, it may be desired that the automatic emergency reporting system 1 be improved to allow for a more appropriate emergency response.

Figure 2:
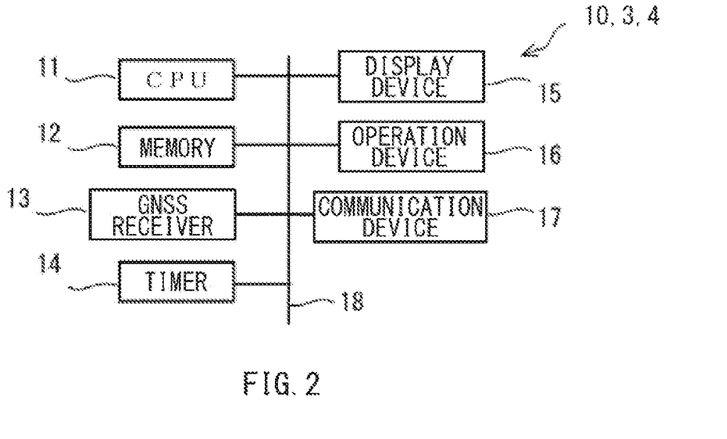
FIG. 2 is an explanatory diagram illustrating a computer that may be used as a server or an operator terminal illustrated in FIG. 1.

FIG. 2 is an explanatory diagram illustrating a computer 10 that may be used as the server 4 or the operator terminal 3 illustrated in FIG. 1.

The computer 10 illustrated in FIG. 2 may include a central processing unit (CPU) 11, a memory 12, a global navigation satellite system (GNSS) receiver 13, a timer 14, a display device 15, an operation device 16, the communication device 17, and a computer network 18 that couples these components. Note that the computer 10 serving as the server 4 may include the CPU 11, the memory 12, the GNSS receiver 13, the timer 14, and the communication device 17. The computer 10 serving as the operator terminal 3 may include an unillustrated microphone and an unillustrated speaker to be used for a phone call.

The communication device 17 may be coupled to the communication network 7 and the local area network 5. In a case where the communication network 7 is coupled to the local area network 5 through a router, for example, only the local area network 5 may be directly coupled to the communication device 17. The communication device 17 may transmit and receive communication data of the computer 10.

The display device 15 may be a liquid crystal monitor, for example. The display device 15 may display a screen for the operator. Non-limiting examples of the display screen of the display device 15 may include an emergency report screen, a phone call screen, and a dispatch request screen.

The emergency report screen may be a screen that displays, for example, presence or absence of an emergency report and details of the emergency report. Non-limiting examples of the details of the emergency report may include a site, i.e., a position of the automobile 2 that has made the emergency report, a report time, and a reported or predicted state about the automobile 2 and the occupant. Presence or absence of another emergency report issued near the automobile 2 may also be displayed, for example.

The phone call screen may be, for example, an outgoing call screen for the automobile 2 from which the emergency report has been received or a mobile terminal of the occupant thereof.

The dispatch request screen may be a request screen for a dispatch team present near the site where an emergency has occurred.

The operation device 16 may be a keyboard, a pointing device, a touch panel, or a button, for example. The operation device 16 may be operated by the operator. The operator may operate the operation device 16 to, for example, switch the display screen of the display device 15.

The GNSS receiver 13 may receive radio waves from GNSS satellites 101 illustrated in FIG. 1, and generate a current time. The GNSS receiver 13 may obtain a position where the computer 10 is installed, together with the current time.

The timer 14 may measure a time period or a time. The time of the timer 14 may be calibrated by the current time of the GNSS receiver 13.

The memory 12 may hold a program and data to be used to cause the computer 10 to serve as the server 4 or the operator terminal 3.

The CPU 11 may read the program from the memory 12 and execute the program. This enables the CPU 11 to serve as a processor that controls overall operation of the server 4 or a processor that controls overall operation of the operator terminal 3.

The CPU 11 serving as the processor of the server 4 may transmit data from the communication device 17 in a case where an access is made from the operator terminal 3 to the communication device 17.

The CPU 11 serving as the processor of the operator terminal 3 may receive an emergency report from the automobile 2, switch the display of the display device 15 in response to the operator's operation, and execute control based on an operation on the display screen. Non-limiting examples of the control based on the operation on the display screen may include control of an outgoing call to the automobile 2 that has made the emergency report or the occupant thereof, control of accessing the server 4 to acquire information held in the memory 12 of the server 4, and control of an outgoing call to a dispatch team for a dispatch request. In one embodiment, the memory 12 of the server 4 may serve as a "server memory".

Figure 3:
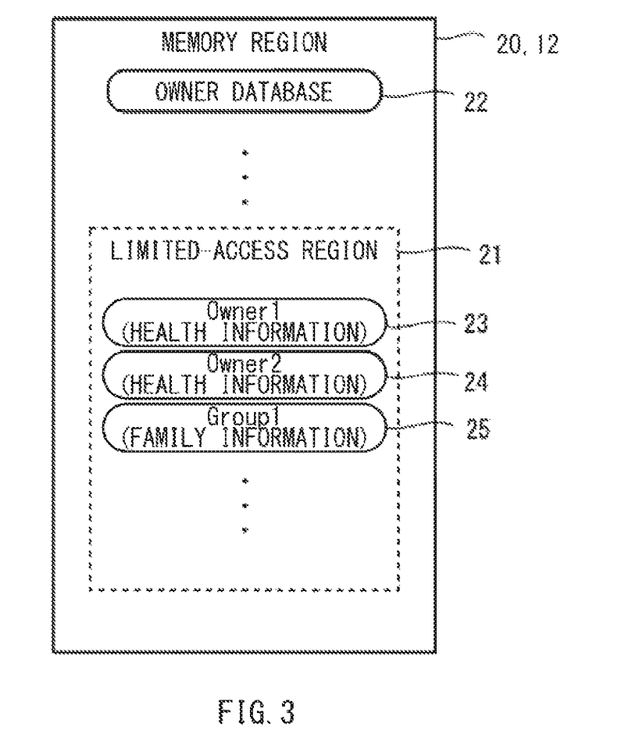
FIG. 3 is an explanatory diagram illustrating a memory region for a memory of the server illustrated in FIG. 1.

FIG. 3 is an explanatory diagram illustrating a memory region 20 for the memory 12 of the server 4 illustrated in FIG. 1.

The memory region 20 of the server 4 illustrated in FIG. 3 may hold an owner database 22, and a plurality of limited-access files to which access from the operator terminal 3 is limited. The owner database 22 may be held in a region to which access from the operator terminal 3 is not limited. The plurality of limited-access files may be held in a limited-access region 21. Non-limiting examples of the files of the limited-access region 21 may include owner files (Owner1 and Owner2) 23 and 24 for respective automobiles 2, and a group file (Group 1) 25 for each occupant group of the automobile 2. The files held in the limited-access region 21 may be in an encoded state in which data thereof is developable with the use of a password.

Figure 4:
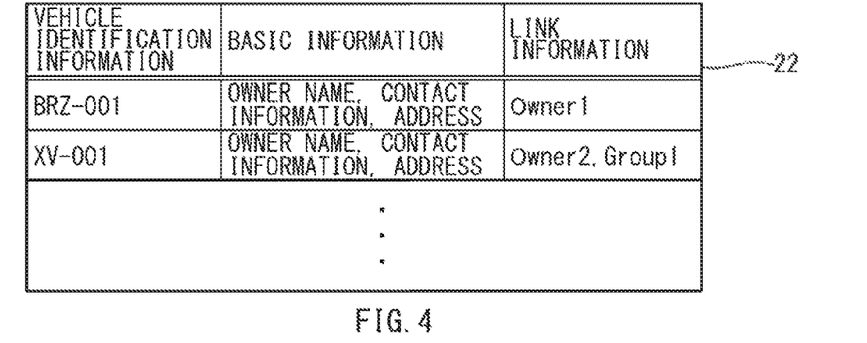
FIG. 4 is an explanatory diagram illustrating an owner database that is held in the memory region illustrated in FIG. 3.

FIG. 4 is an explanatory diagram illustrating the owner database 22 that is held in the memory region 20 illustrated in FIG. 3.

In the owner database 22 illustrated in FIG. 4, information about a plurality of automobiles 2 for which the emergency support center manages emergencies may be held as a plurality of records for the respective automobiles 2.

The record for each automobile 2 may include at least, for example, vehicle identification information to be used to uniquely identify each automobile 2, minimum basic information about the automobile 2 and the owner, and link information for the file of the limited-access region 21 about the automobile 2 and the owner included in the basic information.

The vehicle identification information may be information unique to each automobile 2. For example, a chassis number may be used as the vehicle identification information.

The basic information may include minimum information about the automobile 2 and the owner. The minimum information may include, for example, a model, a vehicle type, a color, or a characteristic appearance to be used to identify the automobile 2, and contact information, an address, and a contact telephone number of the owner. The minimum information may include a part of these pieces of information, or may include information other than these. Note that, in terms of personal information protection, for example, information included in the owner database 22 may be the minimum information to be used to identify the automobile 2 involved in an emergency and make it possible to quickly take an action for rescue of the occupant. Accordingly, the owner database 22 may not include, for example, health information of the owner or health information of a passenger of the automobile 2.

As the link information for the files 23 to 25 of the limited-access region 21, file names or paths of the files 23 to 25 of the limited-access region 21 may be held. File names or paths of a plurality of files may be held as the link information.

In FIG. 3, the owner files 23 and 24 may hold limited-access information for each automobile 2. The limited-access information for each automobile 2 may include the health information of the owner who uses the automobile 2.

The group file 25 may hold limited-access information for each occupant group, such as a family, that may possibly ride the automobile 2. The limited-access information for each occupant group may include, for example, the health information of each occupant included in the occupant group.

The health information about the owner and the passenger may include, for example, a disease history, an underlying health condition, a chronic disease, a medical history, and medication of each person.

The owner files 23 and 24 or the group file 25 may hold, in addition to the health information, personal information other than the basic information, family information, and emergency contact information.

The owner files 23 and 24 or the group file 25 may be, for example, encoded with different passwords for the respective files to be held in the memory 12. A common password may be set for each automobile 2 or for each owner.

The memory region 20 of the server 4 may thus include a region to which access from the operator terminal 3 is limited and a region to which access from the operator terminal 3 is not limited. The general basic information and the detailed personal information may be separately held in the regions with different security levels achieved by access limitation. In one embodiment, the basic information and the personal information may serve as "emergency-related information". The personal information that is held in the limited-access region 21 achieves high confidentiality, saving security, and unauthorized use preventability.

Even if the operator operates the operator terminal 3 to access the server 4 in a situation in which no emergency report has been issued, for example, the operator is unable to check contents, i.e., the limited-access information, of the files 23 to 25 held in the limited-access region 21 of the server 4.

In a case where the operator terminal 3 has received authentication information together with an emergency report from the automobile 2, the operator may acquire the limited-access information from the memory 12 of the server 4, by operating the operator terminal 3 to access the server 4. This enables the operator to acquire the limited-access information held in the server 4 as information related to an emergency.

Figure 5:
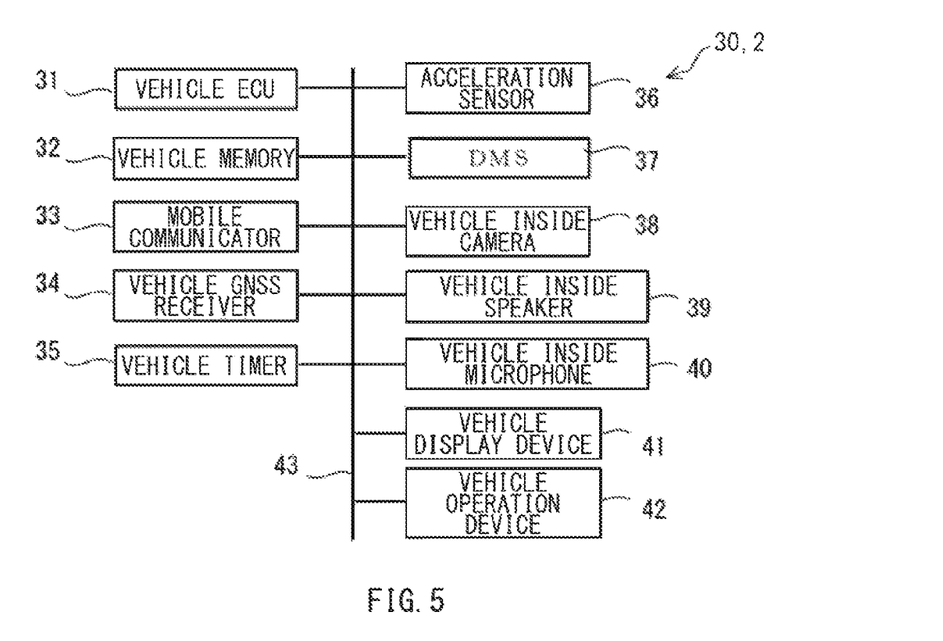
FIG. 5 is an explanatory diagram illustrating a control system of the automobile illustrated in FIG. 1.

FIG. 5 is an explanatory diagram illustrating the control system 30 of the automobile 2 illustrated in FIG. 1.

The control system 30 of the automobile 2 illustrated in FIG. 5 may include a vehicle electronic control unit (ECU) 31, a vehicle memory 32, the mobile communicator 33, a vehicle GNSS receiver 34, a vehicle timer 35, an acceleration sensor 36, an occupant monitoring device (e.g., a driver monitoring system (DMS)) 37, a vehicle inside camera 38, a vehicle inside speaker 39, a vehicle inside microphone 40, a vehicle display device 41, a vehicle operation device 42, and a vehicle network 43 that couple these components.

The vehicle network 43 may be a wired communication network conforming to a controller area network (CAN) or a local interconnect network (LIN), for example, for the automobile 2. The vehicle network 43 may be a communication network such as a local area network (LAN), or may be a combination of such communication networks. The vehicle network 43 may partly include a wireless communication network.

The vehicle GNSS receiver 34, the vehicle timer 35, the vehicle display device 41, the vehicle operation device 42, the vehicle inside speaker 39, and the vehicle inside microphone 40 may be similar to the corresponding components of the computer 10 illustrated in FIG. 2. Note that the vehicle operation device 42 may be, for example, a touch panel that is overlayed on the vehicle display device 41. The vehicle display device 41 may display, for example, a situation of automatic driving of the automobile 2 and an emergency report screen.

The mobile communicator 33 may establish a communication path with the base station 6. The mobile communicator 33 may transmit and receive data to and from the communication device 17 of the operator terminal 3, through the base station 6 and the communication network 7. In one embodiment, the mobile communicator 33 may serve as a "vehicle communicator".

The acceleration sensor 36 may detect an acceleration of the automobile 2. The acceleration sensor 36 may detect a speed of the automobile 2. A sudden stop or collision of the automobile 2 causes an acceleration higher than a usual acceleration.

The vehicle inside camera 38 may capture an image of a vehicle compartment of the automobile 2. The vehicle inside camera 38 may capture an image of only the owner of the automobile 2 or an image of the entire vehicle compartment.

The occupant monitoring device 37 may identify the owner and the passenger riding the automobile 2 and monitor a state of each occupant, on the basis of the image captured by the vehicle inside camera 38. The occupant can doze, look aside, or have an abnormal heart rate. The occupant monitoring device 37 may detect an abnormality about a health state of the occupant on the basis of, for example, the abnormal heart rate.

The vehicle memory 32 may hold a program and data.

The vehicle ECU 31 may read the program from the vehicle memory 32 and execute the program. This enables the vehicle ECU 31 to serve as a processor that controls overall operation, including travel control, of the automobile 2.

The vehicle ECU 31 serving as the processor of the automobile 2 may control travel of the automobile 2 based on the automatic driving, for example.

Collision can be detected by a detection value of the acceleration sensor 36 exceeding a threshold, or an abnormality or irregularity in the health state of the occupant can be detected by the occupant monitoring device 37, for example. In such a case, the vehicle ECU 31 may automatically transmit an emergency report to the operator terminal 3 via the mobile communicator 33 on the basis of the detection.

Figure 6:
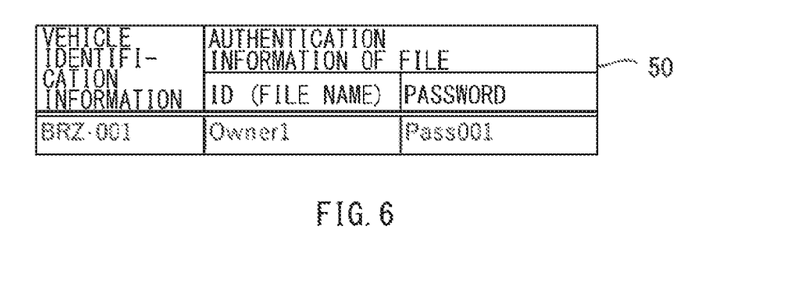
FIG. 6 is an explanatory diagram illustrating authentication information that is held in a vehicle memory illustrated in FIG. 5.

FIG. 6 is an explanatory diagram illustrating authentication information 50 that is held in the vehicle memory 32 illustrated in FIG. 5.

As illustrated in FIG. 6, the vehicle memory 32 holds the authentication information 50 to be used to access the limited-access information held in the memory 12 of the server 4.

In one example, as illustrated in FIG. 6, the vehicle memory 32 may hold the vehicle identification information held in the server 4, a file name or path of an own-vehicle-related file held in the limited-access region 21 of the server 4, and a password to be used to open the file.

The vehicle memory 32 of the automobile 2 may thus not hold information on contents of the own-vehicle-related file. Note that the vehicle memory 32 may hold the information on the contents of the own-vehicle-related file, together with the authentication information 50 to be used to access the server 4.

In a case where the automobile 2 is involved in an emergency and the vehicle ECU 31 transmits an emergency report to the operator terminal 3 via the mobile communicator 33, the vehicle ECU 31 may access the vehicle memory 32 to read the authentication information 50, and transmit the authentication information 50, as the emergency-related information, together with the emergency report.

Figure 7:
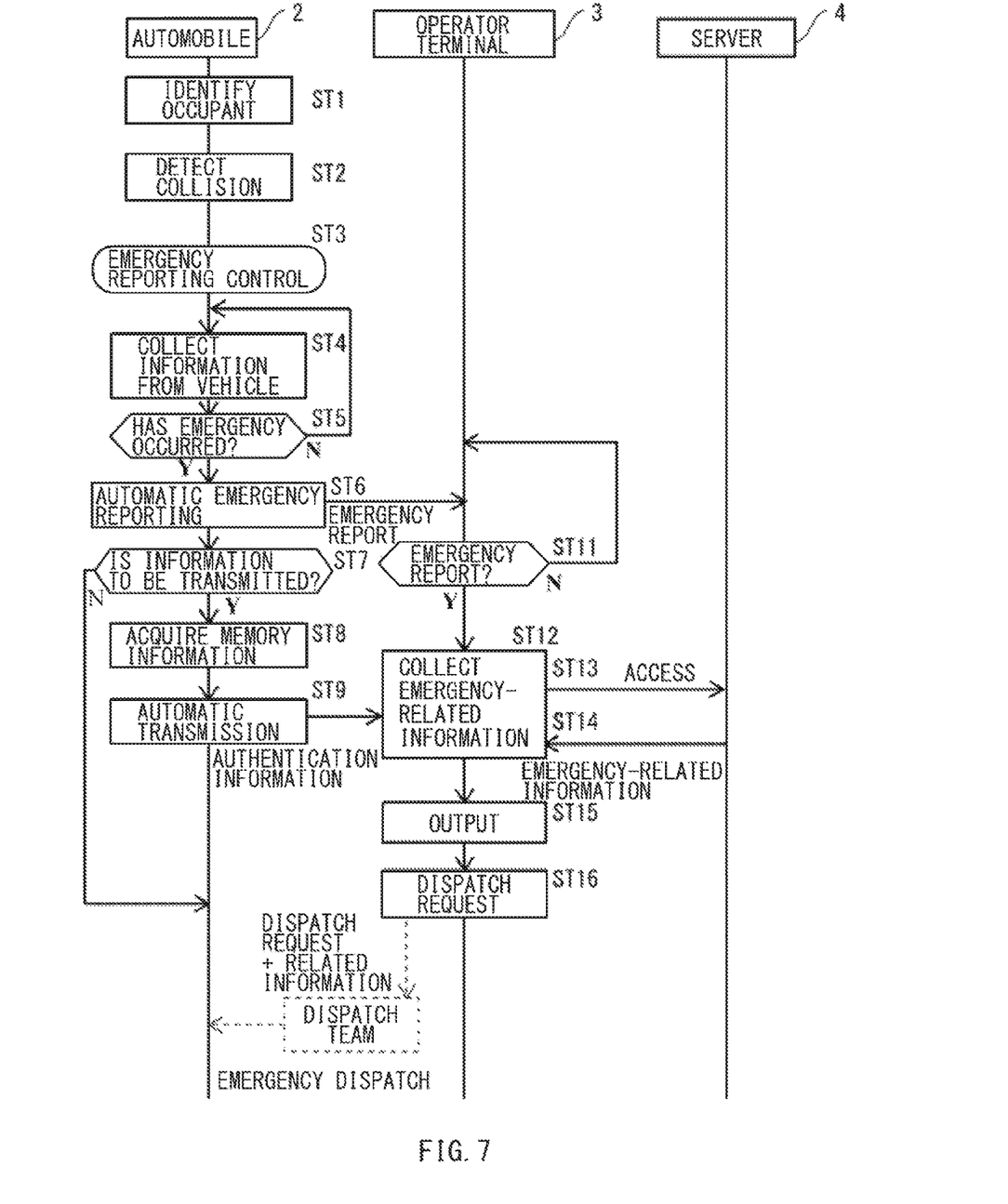
FIG. 7 is a timing chart illustrating an example flow of automatic emergency reporting in the entire automatic emergency reporting system illustrated in FIG. 1.

FIG. 7 is a timing chart illustrating an example flow of automatic emergency reporting in the entire automatic emergency reporting system 1 illustrated in FIG. 1.

FIG. 7 illustrates the automobile 2, the operator terminal 3, and the server 4. Time flows from the top to the bottom.

FIG. 7 illustrates an example of emergency reporting in a case of collision of the automobile 2. Reporting in another emergency may be similar to the reporting in FIG. 7.

In step ST1, the vehicle ECU 31 of the automobile 2 may identify the occupant riding the automobile 2. The vehicle ECU 31 may identify the riding occupant by means of, for example, the occupant monitoring device 37.

In step ST2, the vehicle ECU 31 of the automobile 2 may detect collision of the automobile 2. The vehicle ECU 31 may detect the collision of the automobile 2, for example, if the detection value of the acceleration sensor 36 exceeds the threshold. The vehicle ECU 31 may detect the collision of the automobile 2 by predicting unavoidable collision of the automobile 2.

In step ST3, the vehicle ECU 31 of the automobile 2 may start emergency reporting control on the basis of the detection of the collision of the automobile 2.

In step ST4, the vehicle ECU 31 of the automobile 2 may collect information from the automobile 2 serving as a vehicle. The vehicle ECU 31 may collect information about the state of the occupant after the collision detection, for example, by means of the occupant monitoring device 37. The occupant can be hurt or injured by the collision or can be unconscious.

In step ST5, the vehicle ECU 31 of the automobile 2 may determine whether an emergency for which an emergency report is to be made has occurred. The vehicle ECU 31 may determine whether an emergency for which an emergency report is to be made has occurred, for example, on the basis of a degree of impact applied by the collision, or presence or absence of consciousness or a motion of the occupant, such as the owner. If an emergency for which an emergency report is to be made has occurred (ST5: Y), the vehicle ECU 31 may cause the flow to proceed to step ST6. If an emergency for which an emergency report is to be made has not occurred (ST5: N), the vehicle ECU 31 may cause the flow to return to step ST4. This enables the vehicle ECU 31 to keep monitoring about the state after the collision detection. The vehicle ECU 31 may end this control, without causing the flow to return to step ST4, after elapse of a predetermined period.

In step ST6, the vehicle ECU 31 of the automobile 2 may automatically transmit an emergency report. The vehicle ECU 31 may transmit, to the operator terminal 3 via the mobile communicator 33, an emergency report indicating that the automobile 2 is involved in the emergency due to an accident.

In step ST7, the vehicle ECU 31 of the automobile 2 may determine the necessity to transmit information associated with the emergency report. The vehicle ECU 31 may determine the necessity to transmit the information associated with the emergency report, for example, on the basis of the information collected in step ST4. If the associated information is to be transmitted (ST7: Y), the vehicle ECU 31 may cause the flow to proceed to step ST8. If the associated information does not have to be transmitted (ST7: N), the vehicle ECU 31 may end this control.

In step ST8, the vehicle ECU 31 of the automobile 2 may acquire the held information from the vehicle memory 32 of the automobile 2. The vehicle memory 32 may hold the authentication information 50 illustrated in FIG. 6.

In step ST9, the vehicle ECU 31 of the automobile 2 may automatically transmit the information associated with the emergency report. The vehicle ECU 31 may transmit the authentication information 50 acquired in step ST8 to the operator terminal 3 via the mobile communicator 33. If possible, the vehicle ECU 31 may additionally transmit the information collected in step ST4 to the operator terminal 3. The vehicle ECU 31 may transmit the authentication information 50 held in the vehicle memory 32 to the operator terminal 3 via the mobile communicator 33 upon occurrence of the emergency.

In step ST11, the CPU 11 of the operator terminal 3 may determine whether an emergency report has been received. The operator terminal 3 may receive the emergency report transmitted by the vehicle ECU 31 of the automobile 2 in step ST6. If no emergency report has been received (ST11: N), the CPU 11 of the operator terminal 3 may repeat this process. If an emergency report is received (ST11: Y), the CPU 11 of the operator terminal 3 may cause the flow to proceed to step ST12.

In step ST12, the CPU 11 of the operator terminal 3 may collect information related to the received emergency report.

In step ST13, the CPU 11 of the operator terminal 3 may access the server 4. The server 4 may transmit, from the owner database 22 of the memory region 20, information on the automobile 2 related to the emergency report to the operator terminal 3.

In step ST14, the CPU 11 of the operator terminal 3 may acquire the information related to the received emergency report from the server 4.

In collecting the related information, the CPU 11 of the operator terminal 3 may transmit the authentication information 50 to the server 4 in a case where the authentication information 50 has been received from the automobile 2 by the process of step ST9. The server 4 may open the files 23 to 25 of the limited-access region 21 of the memory region 20 by using the authentication information 50, and transmit information included in the files to the operator terminal 3. In this case, the CPU 11 of the operator terminal 3 is able to receive the information on the occupant, such as the owner, in addition to the basic information of the owner database 22, and acquire the information as a part of the emergency-related information.

In the example embodiment, the automobile 2 may thus serve as a key device for authentication.

In step ST15, the CPU 11 of the operator terminal 3 may output, to the display device 15, the received emergency report and the related information acquired from the server 4 on the basis of the emergency report.

The operator is able to grasp, from the display screen of the operator terminal 3, the health information of the owner, for example, in addition to a situation of the emergency due to the accident. The operator is able to grasp the health information, such as the medical history, of the owner, for example, in addition to the general information about the emergency, and determine the most suitable dispatch team.

In step ST16, the CPU 11 of the operator terminal 3 may output, on the basis of the operator's operation on the operation device 16, a dispatch request to the dispatch team determined as being the most suitable on the basis of, for example, the related information.

In response to the dispatch request, the dispatch team may rush to a location of the automobile 2 from which the emergency report has been received, with the emergency report and the related information, and execute emergency response rescue work, for example. The dispatch team is able to execute more accurate rescue work on the basis of the information on the medical history and the received medication of the owner.

In a case where the emergency-related information acquired from the server 4 includes personal information, such as a name, an address, and a telephone number of a family, the operator may place a phone call to contact the family.

Figure 8:
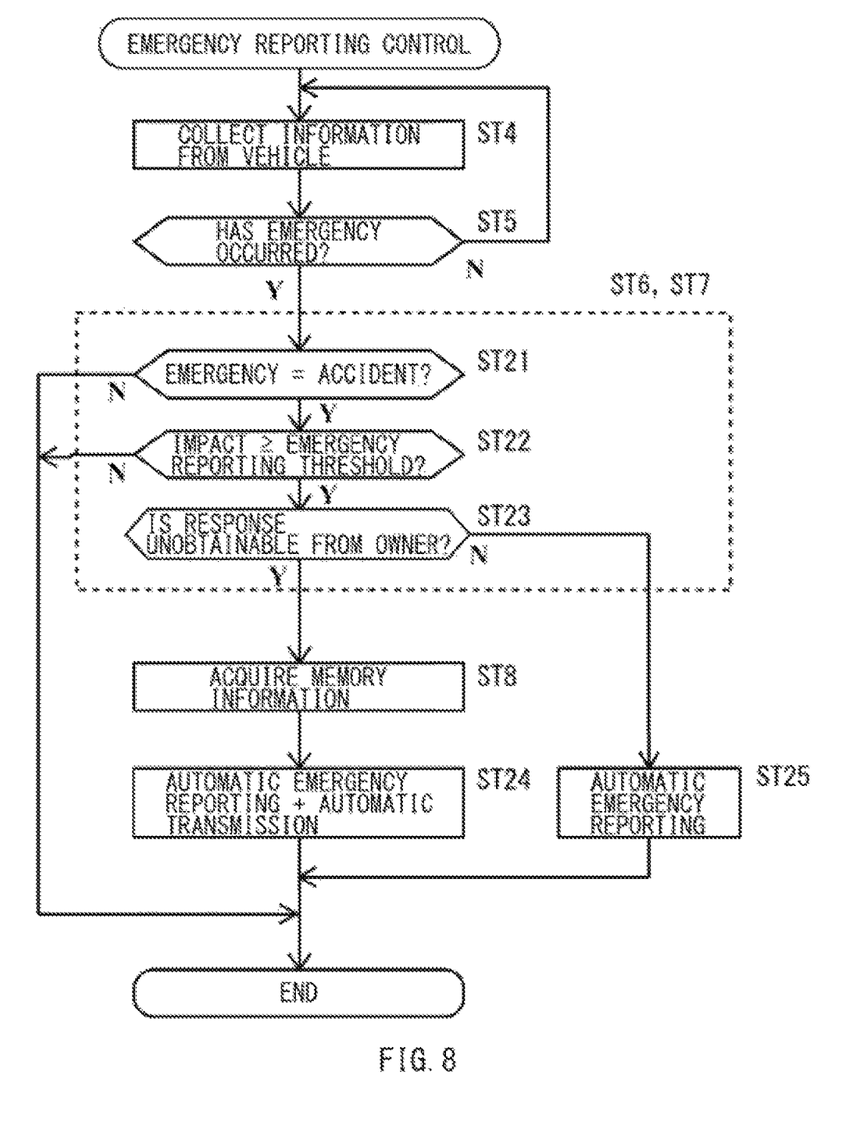
FIG. 8 is a flowchart illustrating an example of emergency reporting control for the automobile, available for the automatic emergency reporting illustrated in FIG. 7.

FIG. 8 is a flowchart illustrating an example of the emergency reporting control for the automobile 2, available for the automatic emergency reporting illustrated in FIG. 7.

The vehicle ECU 31 of the automobile 2 may repeatedly execute the emergency reporting control illustrated in FIG. 8, for example, for the emergency reporting illustrated in FIG. 7.

The processes of step ST4 and step ST5 may be similar to those in FIG. 7. After step ST5, the vehicle ECU 31 may cause the flow to proceed to step ST21.

In step ST21, the vehicle ECU 31 may determine whether the emergency is attributed to an accident. If the detection value of the acceleration sensor 36 is greater than a threshold for determination of a minor collision accident (ST21: Y), for example, the vehicle ECU 31 may determine that the emergency is attributed to an accident, and cause the flow to proceed to step ST22. If the emergency is not attributed to an accident (ST21: N), the vehicle ECU 31 may end this control.

In step ST22, the vehicle ECU 31 may further determine whether the detection value of the acceleration sensor 36 is equal to or greater than an emergency reporting threshold. The emergency reporting threshold may be, for example, higher than the minor collision determination threshold. If the detection value of the acceleration sensor 36 is not equal to or greater than the emergency reporting threshold (ST22: N), the vehicle ECU 31 may end this control. If the detection value of the acceleration sensor 36 is equal to or greater than the emergency reporting threshold (ST22: Y), the vehicle ECU 31 may cause the flow to proceed to step ST23.

In step ST23, the vehicle ECU 31 may determine whether there is a response from the owner. The vehicle ECU 31 may determine whether there is a response from the owner, for example, on the basis of a detection result based on a monitoring image of the occupant monitoring device 37 after the collision detection. In this case, the vehicle ECU 31 may determine that there is no response from the owner if there is no motion of the owner in the monitoring image. In addition, the vehicle ECU 31 may, from the vehicle inside speaker 39, call to the owner by synthesized voice. In this case, the vehicle ECU 31 may determine that there is no response from the owner if a clear response is not obtained via the vehicle inside microphone 40. If there is no response from the owner (ST23: Y), the vehicle ECU 31 may cause the flow to proceed to step ST8. If there is a response from the owner (ST23: N), the vehicle ECU 31 may cause the flow to proceed to step ST25. The vehicle ECU 31 may determine the necessity to transmit the information associated with the emergency report in step ST7 by these processes of step ST21 to step ST23.

In step ST8, the vehicle ECU 31 may acquire the held information from the vehicle memory 32 of the automobile 2. The vehicle memory 32 may hold the authentication information 50 illustrated in FIG. 6. Thereafter, the vehicle ECU 31 may cause the flow to proceed to step ST24.

In step ST24, the vehicle ECU 31 may automatically transmit the authentication information 50 acquired in step ST8, together with the emergency report, to the operator terminal 3 as the information associated with the emergency report, unlike in FIG. 7. The mobile communicator 33 may acquire the authentication information 50 held in the vehicle memory 32 from the vehicle ECU 31, and transmit the emergency report to the operator terminal 3. In this case, the operator terminal 3 is able to receive the authentication information 50 together with the emergency report. Unlike in the case of separately receiving the emergency report and the authentication information 50, the operator terminal 3 does not have to execute a process of associating the emergency report and the authentication information 50 separately received. Thereafter, the vehicle ECU 31 may end this control.

In step ST25, the vehicle ECU 31 may automatically transmit only the emergency report to the operator terminal 3, because there is a response from the owner. In this case, the owner is conscious, and is able to respond to a phone call to be placed by the operator later. Thereafter, the vehicle ECU 31 may end this control.

In a case where the automobile 2 is involved in an emergency due to an accident, the vehicle ECU 31 may thus determine a type of the emergency, an accident level based on collision, and whether the owner is conscious after the accident, to determine the necessity to transmit information associated with an emergency report.

For example, in a case where the impact of the accident is less than the threshold, indicating a minor collision, the vehicle ECU 31 may refrain from transmitting an automatic emergency report to the operator terminal 3. In this case, the owner may cause an emergency report to be made by a manual operation.

In a case where the impact of the accident, or the collision, is equal to or greater than the threshold, and where the owner is not conscious enough to respond after the accident, the vehicle ECU 31 may automatically transmit the authentication information 50 held in the vehicle memory 32 to the operator terminal 3, together with the emergency report.

In a case where the impact of the accident, or the collision, is equal to or greater than the threshold, and where the owner is conscious enough to respond after the accident, the vehicle ECU 31 may automatically transmit only the emergency report to the operator terminal 3.

In some embodiments, automatic transmission to the operator terminal 3 may thus be switched on the basis of the accident level and whether the owner is conscious after the accident. This makes it possible to prevent many emergency reports from being unnecessarily transmitted to the operator terminal 3.

In some embodiments, in a case where the accident level is high and the owner is unconscious after the accident, the operator terminal 3 may be enabled to obtain the associated information together with the emergency report, in consideration that the owner is likely to be in a situation of being unable to report emergency. The mobile communicator 33 of the automobile 2 may, at least only in a case where the automobile 2 is determined as being involved in an emergency, acquire the authentication information 50 held in the vehicle memory 32 and transmit the authentication information 50 to the operator terminal 3.

Note that the vehicle ECU 31 may similarly determine classification also for an emergency other than an accident.

The automobile 2 thus controlling the transmission of the authentication information 50 makes it difficult for the operator terminal 3 to unnecessarily acquire the limited-access information held in the memory 12 of the server 4. This makes it possible to keep the high security level of the limited-access information.

As described above, in the example embodiment, the automobile 2 transmits, in an emergency, the authentication information 50 held in the vehicle memory 32 of the automobile 2 to the operator terminal 3, together with an emergency report. In a case where the operator terminal 3 receives the emergency report from the automobile 2, the operator terminal 3 acquires the limited-access information from the memory 12 of the server 4, as a part of the emergency-related information, by using the authentication information 50 received from the automobile 2. In the example embodiment, it is unnecessary to transmit, from the automobile 2 involved in the emergency to the operator terminal 3, a plurality of pieces of emergency-related information themselves about the automobile 2 and/or the occupant, which tend to have a large amount of information.

In the example embodiment, this enables the automobile 2 involved in an emergency to transmit, to the operator terminal 3, a report that the emergency has occurred and a plurality of pieces of information about the automobile 2 and/or the occupant related to the emergency, by light-load communication processing with short lead time. The operator terminal 3 is able to reliably acquire the plurality of pieces of information about the automobile 2 and/or the occupant related to the automobile 2 involved in the emergency, regardless of a situation of the automobile 2 after the occurrence of the emergency, and use the plurality of pieces of information for emergency response processing to be executed later. Even in a situation in which a part of information is not immediately acquirable from the automobile 2 due to an accident of the automobile 2, for example, the operator terminal 3 is able to reliably acquire the information available for an emergency response. In the example embodiment, it is thus possible to enable the operator terminal 3 to reliably acquire the emergency-related information useful for an emergency response, while suppressing processing load, such as communication load, on the automobile 2 in the transmission of the emergency report.

In some embodiments, the memory 12 of the server 4 may hold the limited-access information about the automobile 2 and/or the occupant, as a part of the plurality of pieces of emergency-related information. Accordingly, the operator terminal 3 may also acquire information to be managed by access limitation, from the memory 12 of the server 4, as a part of the emergency-related information about the automobile 2 and/or the occupant related to the automobile 2 involved in an emergency. Non-limiting examples of the information to be managed by access limitation may include the health information, the personal information, the family information, and the emergency contact information of the owner and/or the passenger of the automobile 2. Non-limiting examples of the health information may include the disease history, the underlying health condition, the chronic disease, and the medication. Moreover, in some embodiments, the authentication information 50 to be used to access the limited-access information may be held in the vehicle memory 32 of the automobile 2, and may be transmitted to the operator terminal 3 only in a case where the automobile 2 is involved in an emergency. In some embodiments, the automobile 2 may be used as a key device, and may be made to transmit the authentication information 50 only in a case where the automobile 2 is involved in an emergency. This makes it possible to securely save the emergency-related information held in the memory 12 of the server 4 in a state in which, for example, strict access limitation is imposed to make the emergency-related information usually hardly acquirable. This makes it possible to achieve information confidentiality, saving security, and unauthorized use prevention.

Second Example Embodiment

Described next is a second example embodiment of the technology. In the example embodiment, emergency reporting control performed by the vehicle ECU 31 of the automobile 2 may be different from that in the foregoing example embodiment. Other points may be similar to those in the foregoing example embodiment, and description thereof is omitted.

Figure 9:
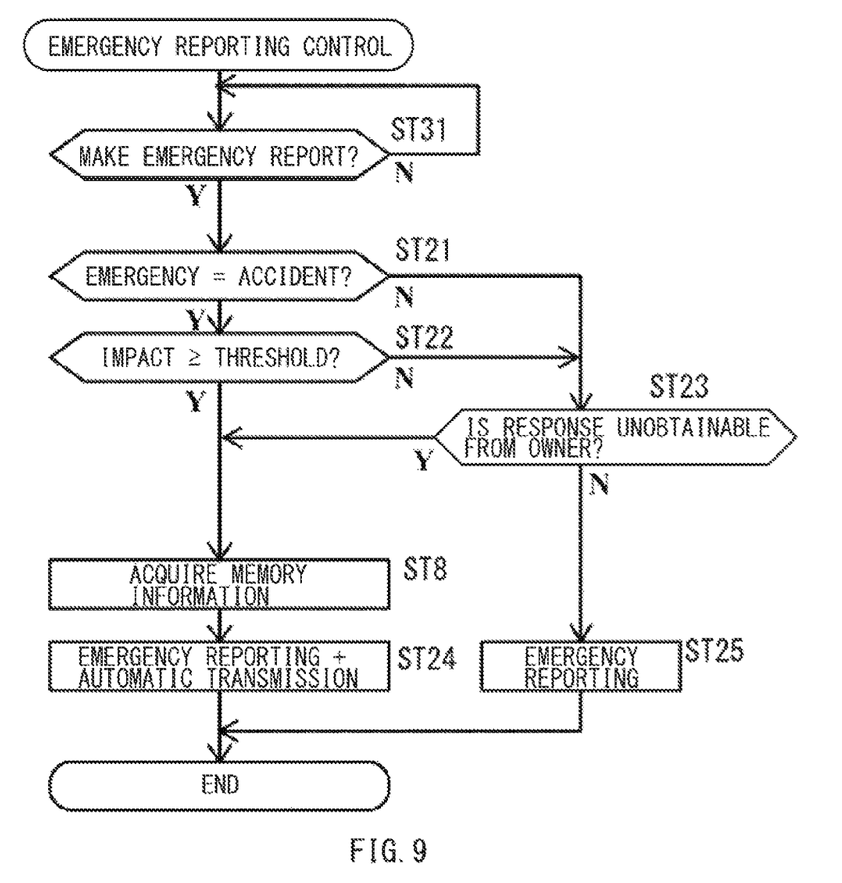
FIG. 9 is a flowchart illustrating emergency reporting control that may be performed by the automobile, according to one example embodiment of the technology.

FIG. 9 is a flowchart illustrating the emergency reporting control that may be performed by the automobile 2, according to the second example embodiment of the technology.

The vehicle ECU 31 of the automobile 2 may repeatedly execute the emergency reporting control illustrated in FIG. 9 for the emergency reporting to the operator terminal 3.

In step ST31, the vehicle ECU 31 may determine whether to make an emergency report to the operator terminal 3. If a detection value at a level corresponding to an accident has been detected in the automobile 2 by the acceleration sensor 36, for example (ST31: Y), the vehicle ECU 31 may determine to make an emergency report to the operator terminal 3, and cause the flow to proceed to step ST21. Also in a case where an emergency other than collision has occurred, the vehicle ECU 31 may determine to make an emergency report to the operator terminal 3, and cause the flow to proceed to step ST21. An example of the case where an emergency other than collision has occurred may be a case where the occupant monitoring device 37 has detected an abnormal state about, for example, a pulse, a blood pressure, or a posture of the owner. If the vehicle ECU 31 does not determine to make an emergency report to the operator terminal 3 (ST31: N), the vehicle ECU 31 may repeat this process until the vehicle ECU 31 determines to make an emergency report.

In step ST21, the vehicle ECU 31 may determine whether the emergency report to the operator terminal 3 is based on an emergency due to an accident. If the emergency is attributed to an accident (ST21: Y), the vehicle ECU 31 may cause the flow to proceed to step ST22. If the emergency is not attributed to an accident (ST21: N), the vehicle ECU 31 may cause the flow to proceed to step ST23.

In step ST22, the vehicle ECU 31 may determine the level of the impact of the accident. Accidents may be classified into, for example, a minor collision with small impact and a severe collision with large impact. In a case of a minor collision, it seems that damage to a vehicle body is less likely to greatly deform the vehicle compartment, and an injury value of the occupant, such as the owner, is often not large. In this case, the occupant seem to be able to determine the necessity to report emergency on his/her own and make an emergency report by a manual operation. In contrast, in a case of a severe collision, it seems that damage to the vehicle body is likely to greatly deform the vehicle compartment, and the injury value of the occupant, such as the owner, tends to be large. In this case, the occupant can be unconscious or unable to move. The vehicle ECU 31 may compare, as the level of the impact of the accident, the detection value of the acceleration sensor 36 with the determination threshold. If the detection value of the acceleration sensor 36 is equal to or greater than the threshold (ST22: Y), the vehicle ECU 31 may determine that the level of the impact of the accident is as high as the threshold or greater, and cause the flow to proceed to step ST8. If the detection value of the acceleration sensor 36 is not equal to or greater than the threshold (ST22: N), the vehicle ECU 31 may determine that the level of the impact of the accident is not as high as the threshold or greater, and cause the flow to proceed to step ST23.

In step ST23, the vehicle ECU 31 may determine whether there is a response from the owner. For example, the vehicle ECU 31 may, from the vehicle inside speaker 39, call to the owner by synthesized voice. In this case, the vehicle ECU 31 may determine that there is no response from the owner if a clear response is not obtained via the vehicle inside microphone 40. If there is no response from the owner (ST23: Y), the vehicle ECU 31 may cause the flow to proceed to step ST8. If there is a response from the owner (ST23: N), the vehicle ECU 31 may cause the flow to proceed to step ST25. The vehicle ECU 31 may determine the necessity to transmit the information associated with the emergency report in step ST7 by these processes of step ST21 to step ST23.

In step ST8, the vehicle ECU 31 may acquire the held information from the vehicle memory 32 of the automobile 2. The vehicle memory 32 may hold the authentication information 50 illustrated in FIG. 6. Thereafter, the vehicle ECU 31 may cause the flow to proceed to step ST24.

In step ST24, the vehicle ECU 31 may automatically transmit the authentication information 50 acquired in step ST8, together with the emergency report, to the operator terminal 3 as the information associated with the emergency report. The mobile communicator 33 may acquire the authentication information 50 held in the vehicle memory 32 from the vehicle ECU 31, and transmit the emergency report to the operator terminal 3. In this case, the operator terminal 3 is able to receive the authentication information 50 together with the emergency report. Unlike in the case of separately receiving the emergency report and the authentication information 50, the operator terminal 3 does not have to execute a process of associating the emergency report and the authentication information 50 separately received. Thereafter, the vehicle ECU 31 may end this control.

In step ST25, the vehicle ECU 31 may automatically transmit only the emergency report to the operator terminal 3, because there is a response from the owner. In this case, the owner is conscious, and is able to respond to a phone call to be placed by the operator later. Thereafter, the vehicle ECU 31 may end this control.

As described above, in some embodiments, the vehicle ECU 31 may, via the mobile communicator 33, acquire the authentication information 50 held in the vehicle memory 32, and transmit an emergency report to the operator terminal 3, only in a case where the automobile 2 is involved in an emergency due to an accident at a predetermined level or greater or in a case where a response from the occupant of the automobile 2 is not obtained. Thus, in other cases, the vehicle ECU 31 may refrain from acquiring the authentication information 50 held in the vehicle memory 32 and transmitting the authentication information 50 to the operator terminal 3 together with the emergency report. The other cases may include a case of manually reporting emergency on the basis of an operation of the occupant, such as the owner, of the automobile 2, and a case where the automobile 2 is merely malfunctioning. In some embodiments, it is possible to prevent the authentication information 50 held in the vehicle memory 32 of the automobile 2 serving as a key device from being excessively transmitted to the operator terminal 3.

Although some embodiments of the technology have been described in the foregoing by way of example with reference to the accompanying drawings, the technology is by no means limited to the embodiments described above. It should be appreciated that modifications and alterations may be made by persons skilled in the art without departing from the scope as defined by the appended claims. The technology is intended to include such modifications and alterations in so far as they fall within the scope of the appended claims or the equivalents thereof.

Figure 10:
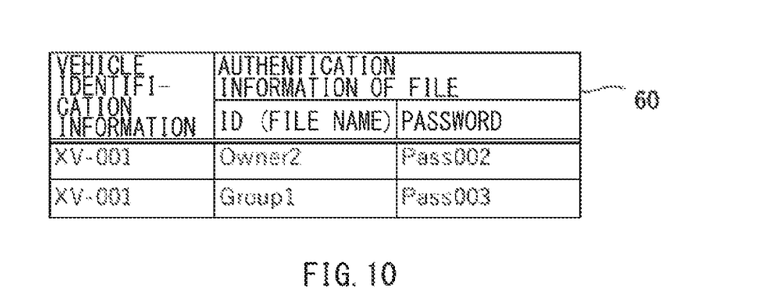
FIG. 10 is an explanatory diagram illustrating an authentication information table that may be held in the vehicle memory, in place of the authentication information illustrated in FIG. 6.

FIG. 10 is an explanatory diagram illustrating an authentication information table 60 that may be held in the vehicle memory 32, in place of the authentication information 50 illustrated in FIG. 6.

In the authentication information table 60 illustrated in FIG. 10, a plurality of pieces of authentication information may be associated with one piece of vehicle identification information of the automobile 2 including the vehicle memory 32. Each piece of authentication information may include a file name or path of the own-vehicle-related file held in the limited-access region 21 of the server 4, and a password to be used to open the file. For example, the authentication information table 60 may include first authentication information and second authentication information. The first authentication information may include a file name or path of a file about the owner of the automobile 2, and a password to be used to open the file. The second authentication information may include a file name or path of a file about a family of the owner, and a password to be used to open the file.

In this case, in an emergency, the vehicle ECU 31 may transmit, via the mobile communicator 33, all of the plurality of pieces of authentication information of the authentication information table 60 to the operator terminal 3. Alternatively, in accordance with a result of determining a situation of the emergency, the vehicle ECU 31 may transmit, via the mobile communicator 33, a part of the plurality of pieces of authentication information of the authentication information table 60 to the operator terminal 3.

For example, in a case where an emergency occurs in a situation in which only the owner is riding the automobile 2, the vehicle ECU 31 may transmit, to the operator terminal 3 via the mobile communicator 33, only the first authentication information serving as a part of the authentication information of the authentication information table 60.

In contrast, in a case where an emergency occurs in a situation in which the owner and the family of the owner are riding the automobile 2, the vehicle ECU 31 may transmit, to the operator terminal 3 via the mobile communicator 33, the first authentication information and the second authentication information serving as all pieces of the authentication information of the authentication information table 60.

As described above, the vehicle memory 32 may hold not only a single piece of authentication information for each automobile 2, but also a plurality of pieces of authentication information for the respective occupants of the automobile 2 and/or for the respective occupant groups of the automobile 2. In this case, the mobile communicator 33 may, in accordance with the situation of the automobile 2 involved in an emergency, select at least a part of the plurality of pieces of authentication information held in the vehicle memory 32, and transmit the selected authentication information to the operator terminal 3. This enables the operator terminal 3 to, in accordance with the situation in which the automobile 2 is involved in the emergency, acquire the limited-access information held in the memory 12 of the server 4 in a state of being limited within a range of use for a response to the emergency.

Each of the CPU 11 illustrated in FIG. 2 and the vehicle ECU 31 illustrated in FIG. 5 is implementable by circuitry including at least one semiconductor integrated circuit such as at least one processor (e.g., a central processing unit (CPU)), at least one application specific integrated circuit (ASIC), and/or at least one field programmable gate array (FPGA). At least one processor is configurable, by reading instructions from at least one machine readable non-transitory tangible medium, to perform all or a part of functions of each of the CPU 11 and the vehicle ECU 31. Such a medium may take many forms, including, but not limited to, any type of magnetic medium such as a hard disk, any type of optical medium such as a CD and a DVD, any type of semiconductor memory (i.e., semiconductor circuit) such as a volatile memory and a non-volatile memory. The volatile memory may include a DRAM and an SRAM, and the nonvolatile memory may include a ROM and an NVRAM. The ASIC is an integrated circuit (IC) customized to perform, and the FPGA is an integrated circuit designed to be configured after manufacturing in order to perform, all or a part of the functions of each of the CPU 11 illustrated in FIG. 2 and the vehicle ECU 31 illustrated in FIG. 5.

The invention claimed is:

1. A vehicle with an emergency reporting function, wherein the vehicle is a part of a vehicle emergency reporting system comprising, in addition to the vehicle:
a server including a server memory configured to hold emergency-related information including non-limited-access information and limited-access information that is related to a vehicle, an occupant of the vehicle, or both, wherein the limited-access information is protected by an access restriction that prevents unauthorized access; and
an operator terminal configured to acquire the emergency-related information in the server memory, wherein the operator terminal is configured to acquire the limited access information from the server memory when the operator terminal has access authorization,
wherein the vehicle comprises:
a vehicle memory configured to store authentication information that provides the operator terminal with the access authorization to acquire the limited-access information from the server memory; and
a vehicle communicator configured to, in response to an emergency in which the vehicle is involved, transmit to the operation terminal, (1) only an emergency report to control the operator terminal to acquire only the non-limited-access information from the server memory, or (2) both the emergency report and the authentication information to control the operation terminal to acquire both the non-limited-access information and the limited-access information from the server memory.

2. The vehicle with the emergency reporting function, according to claim 1, wherein
the occupant comprises a driver and one or more passengers of the vehicle, and
the memory holds, as the limited-access information, health information, personal information, family information, or emergency contact information of the driver, each of the one or more passenger, or both, the health information including a disease history, an underlying health condition, a chronic disease, a medical history, or medication.

3. The vehicle with the emergency reporting function, according to claim 1, wherein the vehicle communicator is configured to, at least in a case where the vehicle is determined as being involved in the emergency, acquire the authentication information held in the vehicle memory and transmit the authentication information to the operator terminal.

4. The vehicle with the emergency reporting function, according to claim 2, wherein the vehicle communicator is configured to, at least in a case where the vehicle is determined as being involved in the emergency, acquire the authentication information held in the vehicle memory and transmit the authentication information to the operator terminal.

5. The vehicle with the emergency reporting function, according to claim 1, wherein, in a case where the emergency is due to an accident, the vehicle communicator is configured to
automatically transmit the authentication information held in the vehicle memory, together with the emergency report, to the operator terminal, on a condition that an impact applied to the vehicle by the accident is equal to or greater than a threshold and that a response from the occupant is not obtained after the accident,
automatically transmit only the emergency report to the operator terminal, on a condition that the impact applied to the vehicle by the accident is equal to or greater than the threshold and that the response from the occupant is obtained after the accident, and
refrain from automatically transmitting the emergency report, on a condition that the impact applied to the vehicle by the accident is less than the threshold.

6. The vehicle with the emergency reporting function, according to claim 2, wherein, in a case where the emergency is due to an accident, the vehicle communicator is configured to
automatically transmit the authentication information held in the vehicle memory, together with the emergency report, to the operator terminal, on a condition that an impact applied to the vehicle by the accident is equal to or greater than a threshold and that a response from the occupant is not obtained after the accident,
automatically transmit only the emergency report to the operator terminal, on a condition that the impact applied to the vehicle by the accident is equal to or greater than the threshold and that the response from the occupant is obtained after the accident, and
refrain from automatically transmitting the emergency report, on a condition that the impact applied to the vehicle by the accident is less than the threshold.

7. The vehicle with the emergency reporting function, according to claim 3, wherein, in a case where the emergency is due to an accident, the vehicle communicator is configured to
automatically transmit the authentication information held in the vehicle memory, together with the emergency report, to the operator terminal, on a condition that an impact applied to the vehicle by the accident is equal to or greater than a threshold and that a response from the occupant is not obtained after the accident,
automatically transmit only the emergency report to the operator terminal, on a condition that the impact applied to the vehicle by the accident is equal to or greater than the threshold and that the response from the occupant is obtained after the accident, and
refrain from automatically transmitting the emergency report, on a condition that the impact applied to the vehicle by the accident is less than the threshold.

8. The vehicle with the emergency reporting function, according to claim 4, wherein, in a case where the emergency is due to an accident, the vehicle communicator is configured to
automatically transmit the authentication information held in the vehicle memory, together with the emergency report, to the operator terminal, on a condition that an impact applied to the vehicle by the accident is equal to or greater than a threshold and that a response from the occupant is not obtained after the accident,
automatically transmit only the emergency report to the operator terminal, on a condition that the impact applied to the vehicle by the accident is equal to or greater than the threshold and that the response from the occupant is obtained after the accident, and
refrain from automatically transmitting the emergency report, on a condition that the impact applied to the vehicle by the accident is less than the threshold.

9. The vehicle with the emergency reporting function, according to claim 1, wherein the vehicle communicator is configured to
acquire the authentication information held in the vehicle memory, and transmit the emergency report and the authentication information to the operator terminal, only in a case where the vehicle is involved in the emergency due to an accident at a predetermined level or greater or in a case where a response from the occupant of the vehicle is not obtained, and transmit the emergency report to the operator terminal without acquiring the authentication information, in other cases including a case of manually reporting emergency on a basis of an operation of the occupant of the vehicle.

10. The vehicle with the emergency reporting function, according to claim 2, wherein the vehicle communicator is configured to acquire the authentication information held in the vehicle memory, and transmit the emergency report and the authentication information to the operator terminal, only in a case where the vehicle is involved in the emergency due to an accident at a predetermined level or greater or in a case where a response from the occupant of the vehicle is not obtained, and transmit the emergency report to the operator terminal without acquiring the authentication information, in other cases including a case of manually reporting emergency on a basis of an operation of the occupant of the vehicle.

11. The vehicle with the emergency reporting function, according to claim 3, wherein the vehicle communicator is configured to acquire the authentication information held in the vehicle memory, and transmit the emergency report and the authentication information to the operator terminal, only in a case where the vehicle is involved in the emergency due to an accident at a predetermined level or greater or in a case where a response from the occupant of the vehicle is not obtained, and transmit the emergency report to the operator terminal without acquiring the authentication information, in other cases including a case of manually reporting emergency on a basis of an operation of the occupant of the vehicle.

12. The vehicle with the emergency reporting function, according to claim 4, wherein the vehicle communicator is configured to acquire the authentication information held in the vehicle memory, and transmit the emergency report and the authentication information to the operator terminal, only in a case where the vehicle is involved in the emergency due to an accident at a predetermined level or greater or in a case where a response from the occupant of the vehicle is not obtained, and transmit the emergency report to the operator terminal without acquiring the authentication information, in other cases including a case of manually reporting emergency on a basis of an operation of the occupant of the vehicle.

13. The vehicle with the emergency reporting function, according to claim 1, wherein the occupant comprises a driver and one or more passengers of the vehicle, the authentication information comprising authentication information pieces corresponding respectively to all or some of the driver and the one or more passengers and an occupant group comprising some of the driver and the one or more passengers, and the vehicle communicator is configured to, in accordance with a situation of the vehicle under the emergency, select at least some of the authentication information pieces, and transmit the selected authentication information pieces to the operator terminal.

14. The vehicle with the emergency reporting function, according to claim 2, wherein the authentication information comprising authentication information pieces corresponding respectively to all or some of the driver and the one or more passengers and an occupant group comprising some of the driver and the one or more passengers, and the vehicle communicator is configured to, in accordance with a situation of the vehicle under the emergency, select at least some of the authentication information pieces, and transmit the selected authentication information pieces to the operator terminal.

15. The vehicle with the emergency reporting function, according to claim 3, wherein the occupant comprises a driver and one or more passengers of the vehicle, the authentication information comprising authentication information pieces corresponding respectively to all or some of the driver and the one or more passengers and an occupant group comprising some of the driver and the one or more passengers, and the vehicle communicator is configured to, in accordance with a situation of the vehicle under the emergency, select at least some of the authentication information pieces, and transmit the selected authentication information pieces to the operator terminal.

16. The vehicle with the emergency reporting function, according to claim 4, wherein the authentication information comprising authentication information pieces corresponding respectively to all or some of the driver and the one or more passengers and an occupant group comprising some of the driver and the one or more passengers, and the vehicle communicator is configured to, in accordance with a situation of the vehicle under the emergency, select at least some of the authentication information pieces, and transmit the selected authentication information pieces to the operator terminal.

17. A vehicle emergency reporting system comprising:

a server including a server memory configured to hold emergency-related information including non-limited-access information and limited-access information that is related to a vehicle, an occupant of the vehicle, or both, wherein the limited-access information is protected by an access restriction that prevents unauthorized access;

an operator terminal configured to acquire the emergency-related information held in the server memory, wherein the operator terminal is configured to acquire the limited access information from the server memory when the operator terminal has access authorization; and a vehicle comprising:

a vehicle memory configured to store authentication information that provides the operator terminal with the access authorization to acquire the limited-access information from the server memory;

a vehicle communicator configured to, in response to an emergency in which the vehicle is involved, transmit only an emergency report, or both the emergency report and the authentication information, to the operator terminal, wherein the operator terminal is configured to:

in response to receiving only the emergency report from the vehicle, acquire only the non-limited-access information from the server memory; and in response to receiving both the emergency report and the authentication information from the vehicle, acquire both the non-limited-access information and the limited-access information from the server memory.

18. A vehicle with an emergency reporting function, the vehicle being configured to, in response to determining that the vehicle is involved in an emergency, transmit an emergency report to an operator terminal, the vehicle comprising:
 a vehicle memory configured to hold authentication information to be used to perform the emergency reporting function;
 a vehicle electronic control unit configured to determine that the vehicle is involved in an emergency caused by an impact applied to the vehicle by an accident, and determine that the impact is equal to or greater than a threshold; and
 a vehicle communicator configured to:
  in response to determining that the vehicle is involved in the emergency and that the impact is equal to greater than the threshold, transmit an emergency report and the authentication information to the operator terminal, wherein the operator terminal is configured to, based on the emergency report and the authentication information, access a memory, outside the vehicle, holding emergency-related information including limited-access information, to acquire the emergency-related information including the limited access information, and wherein the limited-access information is related to the vehicle, an occupant of the vehicle, or both and is protected by an access restriction that prevents the operator terminal from accessing the limited access information without the authentication information; and
  in response to determining that the vehicle is involved in the emergency and that the impact is less than the threshold, transmit only the emergency report to the operator terminal, wherein the operator terminal is configured to, based on the emergency report, access the memory to acquire the emergency-related information except the limited-access information.

* * * * *